United States Patent
Hagemeyer et al.

(10) Patent No.: US 6,197,275 B1
(45) Date of Patent: *Mar. 6, 2001

(54) BISMUTH-CONTAINING CATALYSTS

(75) Inventors: Alfred Hagemeyer, Rheine; Andreas Püttner, Frankfurt; Martin Trömel, Karben, all of (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/911,455

(22) Filed: Aug. 14, 1997

(30) Foreign Application Priority Data

Aug. 23, 1996 (DE) .................. 196 34 192

(51) Int. Cl.[7] .................. C01B 7/01; C01B 7/04; B01J 23/18
(52) U.S. Cl. .................. 423/502; 423/507; 502/353; 502/340; 502/344; 502/302; 502/303
(58) Field of Search .................. 502/353, 302, 502/303, 340, 344; 423/502, 507

(56) References Cited

U.S. PATENT DOCUMENTS

| | | | |
|---|---|---|---|
| 2,191,981 | * | 2/1940 | Jahn .................. 423/502 |
| 2,448,255 | * | 8/1948 | Benedictis et al. .................. 423/502 |
| 3,907,713 | * | 9/1975 | Grasselli et al. .................. 564/420 |
| 4,351,819 | * | 9/1982 | Riegel et al. .................. 423/488 |
| 4,482,644 | * | 11/1984 | Beyerlein et al. .................. 502/303 |
| 4,503,166 | * | 3/1985 | Beyerlein et al. .................. 502/303 |
| 4,959,202 | * | 9/1990 | Minet et al. .................. 423/502 |
| 5,154,911 | * | 10/1992 | Benson et al. .................. 423/502 |
| 5,689,005 | * | 11/1997 | Hagenmeyer et al. .................. 564/420 |

FOREIGN PATENT DOCUMENTS

| | | | |
|---|---|---|---|
| 761 594 | | 9/1996 | (EP) . |
| 0 761 307 | * | 12/1997 | (EP) .................. 423/502 |
| 2297043 | | 7/1996 | (GB) . |
| 6711302 | * | 8/1967 | (NL) .................. 423/502 |
| 91/06505 | | 5/1991 | (WO) . |

OTHER PUBLICATIONS

Itoh et al, Solid State Ionics 49, (1991) pp. 57–62.*

* cited by examiner

Primary Examiner—Ngoc-Yen Nguyen
(74) Attorney, Agent, or Firm—Keil & Weinkauf

(57) ABSTRACT

The active phase of a catalyst composition contains at least one bismuth oxide compound in which bismuth is present at least partly in oxidation state +5, the bismuth oxide compound furthermore containing at least one basic metal component stabilizing the oxidation state +5, and said catalyst composition is used in oxidation and dehydrogenation reactions under heterogeneous catalysis, in particular the preparation of chlorine from hydrogen chloride.

13 Claims, 2 Drawing Sheets

BISMUTH-CONTAINING CATALYSTS

FIELD OF INVENTION

The present invention relates to catalysts containing bismuth oxide compounds, their use in oxidation and dehydrogenation reactions under heterogeneous catalysis, processes for the preparation of chlorine using these catalysts and novel barium bismuth oxide phases and processes for their preparation.

BACKGROUND OF THE INVENTION

In many chemical reactions, for example the phosgenation of diamines for the preparation of isocyanates for polyurethane synthesis, or in vinyl chloride production, HCl is obtained in large amounts as a byproduct. There are various possibilities for utilizing the HCl obtained: marketing, further processing, for example in oxychlorination, disposal by neutralization, use for the preparation of inorganic chlorides or recycling to give chlorine. Since the trend in the market for HCl is difficult to assess, and in view of a steadily increasing amount of HCl from production processes, there is a considerable demand for HCl recycling processes in which chlorine is recovered as the desired substance.

An established recycling process is, for example, electrolysis of HCl or $CuCl_2$ by the Westvaco process, as described by J. Gordon, Chem. Eng. (1953), 187; and Anon, Chem. Eng. (1960), 63. However, the high energy costs are the disadvantage aspect of this process.

The prior art long ago disclosed various processes for the preparation of chlorine by HCl oxidation. The oldest is the process developed by Deacon in 1868 for the direct and continuous reaction of HCl with air or oxygen over a copper chloride catalyst (cf. for example the review article by Kepinski, J., Tilly, J., Katucki, K. in Przem. Chem. 57(1) (1978), 14–17 and Kepinski, J., Kalucki, K. in Szczecin. Tow. Nauk., Wydz. Nauk. Mat. Tech. 9, 1973, 37–49). The reaction is equilibrium-limited so that the conversion is not more than 75%. The product stream thus also contains HCl, $H_2O$ and air/oxygen in addition to $Cl_2$. This necessitates subsequent, expensive working up of the $Cl_2$ present, serious corrosion problems occurring owing to the aqueous hydrochloric acid present in the product gas.

A modified, large-scale industrial process is the Shell-Deacon process, in which HCl is oxidized with air to give chlorine by heterogeneous catalysis over a supported $CuCl_2$/$KCl/LaCl_3$ catalyst in a fluidized-bed reactor with a yield of about 77%. This process is described, for example, by J. Th. Quant et al. in The Chemical Engineer, July/August 1963, page 224.

A further process which was previously used industrially is the Weldon process, in which manganese dioxide is used for oxidizing HCl. However, the chlorine yield was only about 30% since half the HCl used was lost in the form of $CaCl_2$ during the recycling of the $MnCl_2$ to $MnO_2$ with the use of $Ca(OH)_2$ and $O_2$.

In the Kel chlorine process from Kellog, HCl is converted into chlorine with nitrosyl sulfuric acid at high pressure and elevated temperature. Here too, the problem of corrosion leads to the use of expensive materials and hence to high capital costs.

FR 14 97 776 describes a variant of the Deacon process, in which the catalyst is used in the form of a carborundum-$CuCl_2$-KCl salt melt (supported liquid phase). At the prevailing reaction temperatures of about 400° C., however, a pronounced discharge of the volatile copper chlorides and hence catalyst losses and contamination of the line sections downstream of the reactor occur in this process.

A further variant of the Deacon process is the Mitsui-Toatsu process, in which HCl is oxidized in a fluidized bed over $Cr_2O_3/SiO_2$ catalysts, the HCl conversion being from 75 to 80%. This process is described in EP 0 184 413, EP 0 277 332, EP 0 331 465, EP 0 465 243 and JP 62 254 846. The disadvantage of this process is the high toxicity of the chromium contained in the $Cr_2O_3$ catalysts used.

In the preparation of chlorine by HCl oxidation, a distinction may be made between processes involving a steady-state reaction and those involving a nonsteady-state reaction. In the conventional, steady-state reaction, the HCl-containing feed together with an oxygen-containing gas and possibly further dilution gases is brought into contact continuously as a function of time with the catalyst bed, some of the HCl present being oxidized to $Cl_2$ and $H_2O$, and the reaction products leave the reactor continuously together with unconverted HCl, $O_2$ and carrier gas. Since the reaction is equilibrium-limited, only partial conversion is possible.

In the nonsteady-state processes known from the prior art, the HCl oxidation is carried out in two steps, the catalyst acting as a material reservoir, or more precisely as a chlorine reservoir. In the loading step, the catalyst is chlorinated with HCl and its oxidic active component phase is converted into a chloride phase and water. After a short flushing phase with inert gas, an oxygen-containing gas flows over the latent catalyst in the second step. Chlorine is liberated and the oxidic phase is formed again.

DE 40 04 454 describes a process for obtaining chlorine by oxidation of HCl over two process stages with the use of a transport catalyst. In the first stage, an HCl gas stream is passed through a fluid bed of copper oxides and NaCl, which are applied to a suitable carrier, and a complex chloride is formed by reaction. After removal of the fluid bed for dechlorination in a second reactor, the oxidized transport catalyst is recycled with injection of $O_2$ and $N_2$. U.S. Pat. No. 4,959,202 and EP 04 74 763 likewise describe an unsteady-state process which is carried out in two reactors and in which the HCl loading of the catalyst as well as the dechlorination is effected in the fluidized bed.

WO 91/06505 and U.S. Pat. No. 5,154,911 describe a modified Deacon process with a nonsteady-state reaction with the use of a catalyst which comprises a) a transition metal oxide selected from $MnO_2$, $Co_2O_3$, $Co_3O_4$, $Cr_2O_3$, NiO, $Ni_2O_3$, $Mo_2O_3$, CuO and combinations thereof, b) an alkali metal chloride, selected from LiCl, NaCl, KCl and combinations thereof, c) a promoter, selected from $LaCl_3$, $PrCl_3$, $Pr_2O_3$ and combinations thereof.

The process comprises a chlorination and an oxidation step and is carried out in a fluidized-bed or fixed-bed reactor, and, if required, the catalyst bed may be exchanged between the reaction zones. A similar process for the use of a fixed-bed reactor is described in EP 0 500 728.

DE 43 36 404 likewise describes a modified Deacon process involving a nonsteady-state reaction. It is proposed to dry the HCl gas used by means of a molecular sieve in order to bind the water of reaction formed during the loading phase. Pure oxygen at from 1.0 to 50 bar and from 100 to 500° C. is to be used for the oxidation. The catalysts proposed are manganese oxides and vanadium oxides. The high volatility of vanadyl chlorides and the excessively high activity of $MnO_2$ are to be regarded as problematic in this process, so that chlorine formation is to be expected as early as during the loading phase. Furthermore, the corrosion resistance of the proposed zeolite molecular sieves is questionable. Owing to the high acidity of the zeolites, it must be assumed that there will be considerable HCl adsorption onto the molecular sieve, which HCl forms hydrochloric acid with water also absorbed and attacks the carrier.

H. Y. Pan, R. G. Minett, S. W. Benson and T. T. Tsotsis, Ind. Eng. Chem. Res. 33 (1994), 2996–3003, describe a reactor concept involving coupling of two alternately operated fluidized-bed reactors, a supported $CuCl_2$-NaCl system being used as the catalyst.

The known processes thus have specific disadvantages which arise in particular from incomplete conversion of the hydrogen chloride used and the corrosion problems which therefore arise or the necessity of production processes which employ complicated apparatus and are thus expensive.

BRIEF SUMMARY OF THE INVENTION

It is an object of the present invention to provide suitable catalysts, with the aid of which problems known from the prior art in the oxidation of HCl can be overcome. In particular, the catalysts should permit the preparation of $Cl_2$ with an improved space-time yield.

We have found that this object is achieved by providing catalysts whose active phase contains one or more bismuth oxide compounds which have an oxygen reservoir function.

The present invention therefore relates to catalyst compositions whose active phase contains at least one bismuth oxide compound in which bismuth is present at least partly in oxidation state +5, the bismuth oxide compound furthermore containing at least one basic metal component stabilizing the oxidation state +5.

DETAILED DESCRIPTION OF THE INVENTION

Figure 1:
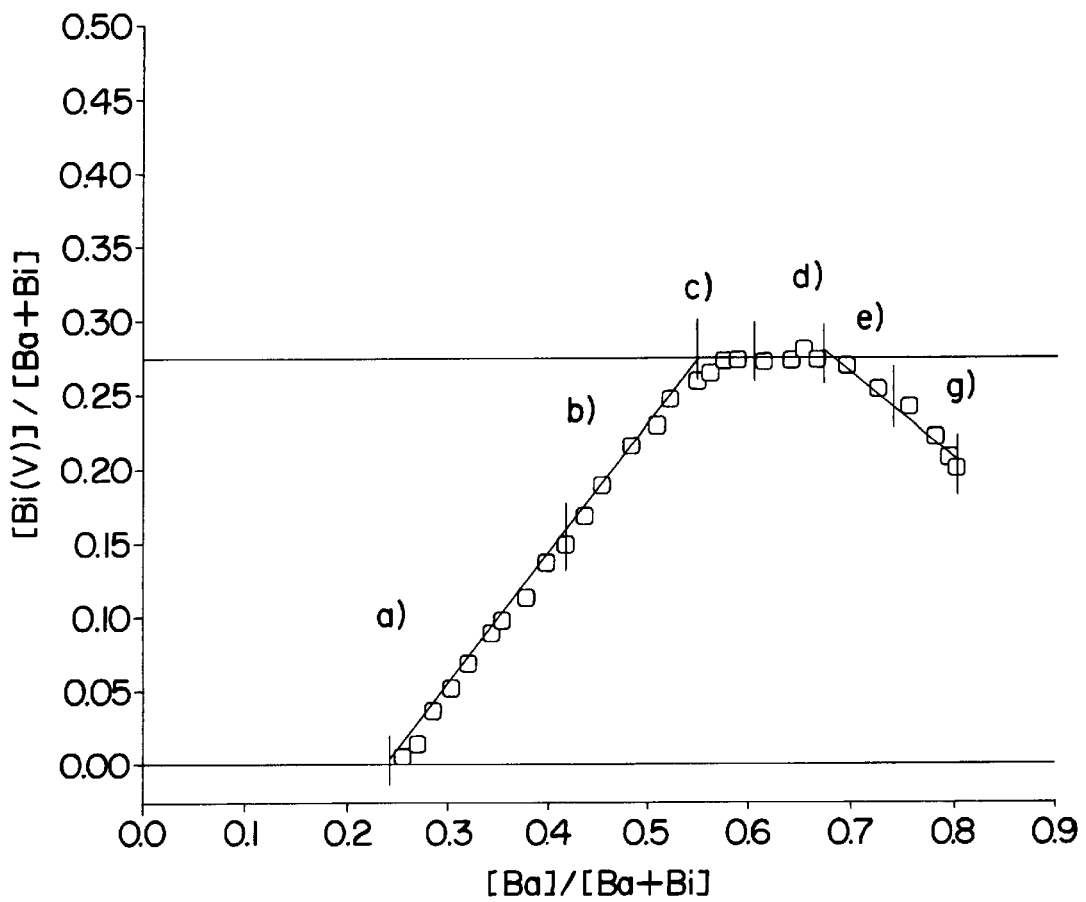
FIG. 1 shows the ration of Bi+5 content, based on the total heavy atom content (y axis) to the Ba content, based on the total heavy atom content, for the individual phases.

An essential feature of the novel catalysts is the use of bismuth oxide compounds in which Bi is present at least partly in oxidation state +5 and said catalysts therefore have a high oxidation potential, resulting in high catalyst activity.

The amount of Bi +5 is preferably from about 5 to 90, particularly preferably from about 20 to 80, % by weight, based on the total bismuth content.

A strongly basic environment is required for stabilizing the high oxidation state of +5. Alkali metals, alkaline earth metals and rare earth metals are suitable for this purpose. In a preferred embodiment, the catalyst contains one or more of the elements Li, Na, K, Sr, Ba, Cs, Y and La. Depending on the basicity of these components, a different amount of basic additives is required.

Particularly preferred catalysts are those in which the active phase contains at least one compound of the general formula $KBi_yO_z$ where y is from 0.5 to 2 and z is from 1.25 to 5.5, in particular y/z being from about 0.4 to about 0.36;

or of the general formula:

$BaBi_yO_z$ where y is from 0.17 to 3 and z is from 1.43 to 5.6, in particular y/z being from about 0.12 to about 0.54, in each case at least part of the Bi being present in oxidation state +5.

The active phase of the catalyst may, if required, contain promoters, in particular from main group 1, 2 and/or 4 and from subgroup 4 and/or 6 of the Periodic Table, which reinforce the catalyst effect. Examples of these are Si, Ge, Ti and/or Cr.

The preparation of the novel bismuth oxide catalysts is carried out in a manner known per se, and both wet-chemical methods, such as precipitation or impregnation, and solid-state reactions, for example calcination, may be used. Starting materials which may be used are, for example, carbonates, hydroxides, oxides, peroxides, nitrates and acetates. The solids prepared in this manner are then processed in a manner known per se to give the catalytically active materials. Processes for the preparation of catalysts are described, for example, in Ullmanns Enzyklopadie der technischen Chemie, 3rd edition, Vol. 9, page 271 et seq. (1957).

In a special embodiment, catalysts containing barium bismuth oxide compounds are prepared. The preparation of some barium bismuth oxide compounds by reacting stoichiometric mixtures of barium carbonate and/or barium nitrate and bismuth oxide is described by M. Itho et al., Solid State Ionics 49, (1991), 57–62.

The following compounds are described by Itoh:

| | |
|---|---|
| $BaBiO_3$ | $(\hat{=} Ba_1Bi_1O_3)$ |
| $Ba_{1.05}Bi_{0.95}O_{2.998}$ | $(\hat{=} Ba_1Bi_{0.905}O_{2.855})$ |
| $Ba_{1.10}Bi_{0.90}O_{2.994}$ | $(\hat{=} Ba_1Bi_{0.818}O_{2.722})$ |
| $Ba_{1.15}Bi_{0.85}O_{2.989}$ | $(\hat{=} Ba_1Bi_{0.739}O_{2.599})$ |
| $Ba_{1.20}Bi_{0.80}O_{2.984}$ | $(\hat{=} Ba_1Bi_{0.667}O_{2.487})$ |
| $Ba_{1.25}Bi_{0.75}O_{2.972}$ | $(\hat{=} Ba_1Bi_{0.600}O_{2.378})$ |
| $Ba_{1.30}Bi_{0.70}O_{2.970}$ | $(\hat{=} Ba_1Bi_{0.538}O_{2.285})$ |
| $Ba_{1.33}Bi_{0.67}O_{2.950}$ | $(\hat{=} Ba_1Bi_{0.504}O_{2.218})$ |
| $Ba_{1.40}Bi_{0.60}O_{2.880}$ | $(\hat{=} Ba_1Bi_{0.429}O_{2.057})$ |
| $Ba_{1.425}Bi_{0.575}O_{2.862}$ | $(\hat{=} Ba_1Bi_{0.404}O_{2.008})$ |
| $Ba_{1.45}Bi_{0.55}O_{2.825}$ | $(\hat{=} Ba_1Bi_{0.379}O_{1.948})$ |
| $Ba_{1.475}Bi_{0.525}O_{2.788}$ | $(\hat{=} Ba_1Bi_{0.355}O_{1.890})$ and |
| $Ba_{1.50}Bi_{0.50}O_{2.753}$ | $(\hat{=} Ba_1Bi_{0.333}O_{1.835})$ |

A general process for the preparation of the novel barium bismuth oxide catalysts comprises reacting one or more barium compounds, in particular barium nitrate, oxide, peroxide, hydroxide or carbonate, with one or more bismuth compounds, in particular bismuth oxide, nitrate, carbonate or hydroxide, it being possible to carry out the reaction by a wet-chemical method or as a solid-state reaction.

The solid-state reaction with the use of barium carbonate and/or barium peroxide and of bismuth peroxide is particularly preferred for the preparation of the novel barium bismuth oxide catalysts. For this purpose, for example, $BaCO_3$ and $Bi_2O_3$ are homogenized in stoichiometric amounts in acetone and calcined at from 700 to 900° C., preferably at about 800° C., for 3 hours. The subsequent cooling is carried out extremely slowly at cooling rates of 1° C./min, in order to achieve maximum oxidation of the bismuth.

The resulting catalytically active barium bismuth oxide compounds have a composition of the general formula $BaBi_yO_z$, where y is from 0.17 to 3 and z is from 1.43 to 5.6. Their bismuth content is from about 25 heavy atom percent (about 16% by weight) to about 90 heavy atom percent. According to the invention, the formation of the following novel phases was also observed:

a) $BaBi_3O_{5.6}$-$BaBi_{1.33}O_{3.4}$ phase having a pseudocubic perovskite structure;
b) $BaBi_{1.32}O_{3.41}$-$BaBi_{0.8}O_{3.04}$ phase having a monoclinic perovskite superlattice;
c) $BaBi_{0.79}O_{3.04}$-$BaBi_{0.7}O_3$ phase having a rhombohedral perovskite superlattice;
d) $BaBi_{0.69}O_3$-$BaBi_{0.41}O_{1.95}$ phase having an elpasolite structure;
e) $BaBi_{0.4}O_{1.84}$-$BaBi_{0.33}O_{1.82}$ phase having a tetragonal perovskite superlattice;
f) $BaBi_{0.32}O_{1.82}$-$BaBi_{0.28}O_{1.68}$ mixed phase of bismuthate having a tetragonal perovskite superlattice and a hexagonal phase;
g) $BaBi_{0.27}O_{1.68}$-$BaBi_{0.17}O_{1.43}$ phase having a hexagonal structure.

The stated phases eliminate oxygen reversibly above about 550° C. Complete reduction of the Bi +5 present to Bi +3 takes place at the same time.

The advantages of the barium bismuth oxide catalysts is the described simple preparation from economical starting materials which can generally be used in industrial purity. Furthermore, the catalysts obtained are nonhygroscopic and are insoluble in most organic solvents. The barium-rich catalysts are insoluble in $HNO_3$ and $H_2SO_4$. Advantageously, no corrosion problems occur in the case of the bismuth oxide compounds described. Owing to the high density and the possibility of preparing coarse-particle products, the novel catalysts are easy to handle and to transport.

The present invention furthermore relates to processes for the preparation of chlorine by oxidation of hydrogen chloride using one or more of the abovementioned catalysts.

For this purpose, the novel catalysts may be used as unsupported catalysts or, before use, may be mixed with a binder or applied to an inert carrier. Suitable carriers for this purpose are conventional substances, such as oxides, in particular silicates, aluminosilicates, zeolites, aluminas, zirconium oxide, carbides, such as SiC, nitrides, such as $Si_3N_4$, nonvolatile chlorides, eg. NaCl, KCl, $CaCl_2$ and $MgCl_2$, or mixtures thereof. Preferred carriers are $SiO_2$, SiC and $Si_3N_4$.

The high activity of the bismuth oxide compounds in the oxidation of hydrogen chloride is based on their content of bismuth in the oxidation state +5, which leads to very rapid oxidation of hydrogen chloride, Bi +5 simultaneously being reduced to Bi +3. If further hydrogen chloride were to be fed in after complete reduction of the Bi +5 to Bi +3, there would be a danger of an undesirable further reaction to give the corresponding bismuth +3 oxychlorides, eg. BiOCl, and alkali metal or alkaline earth metal chlorides, such as $BaCl_2$. Since these can no longer be converted with oxygen into the novel oxides, the catalyst would then no longer be capable of regeneration. By means of a suitable reaction, it is therefore necessary to avoid the further reaction described. This problem is solved by only partly reducing the catalyst, i.e. terminating the reaction before the average oxidation state of the bismuth has decreased to +3. By suitable metering of hydrogen chloride and/or oxygen and, if required, by the choice of a suitable reactor type, a local excess of hydrogen chloride is avoided, as described in more detail below.

The oxidation of hydrogen chloride for the preparation of chlorine can be carried out using the novel catalysts in various process variants, a distinction generally being made between a steady-state and a nonsteady-state reaction. The catalyst is suitable for both process reactions.

In the steady-state reaction, the hydrogen chloride feed, together with an oxygen-containing gas and possibly further diluent gases, eg. argon or nitrogen, is brought into contact with the catalyst bed continuously as a function of time, some of the hydrogen chloride being oxidized to chlorine and water, which likewise leave the reactor continuously together with converted hydrogen chloride and oxygen. In the steady-state reaction, the novel catalyst can be used as a fixed bed, fluidized bed or moving bed or fluid bed. However, since the highly exothermic oxidation of hydrogen chloride in a fixed bed may give rise to problems with heat removal, the reaction may be more advantageous in a fluidized bed or moving bed or fluid bed.

In the nonsteady-state reaction, the process is divided into a cycle comprising two steps, which are repeated continuously. Separation process and heat exchange are integrated in the reactor, leading to a saving of working-up steps, apparatuses and energy. In the nonsteady-state Deacon processes according to the prior art, as described in DE 4 004 454, U.S. Pat. No. 4,959,202, WO 91/06505 (corresponding to U.S. Pat. No. 5,154,911 or EP 0 500 728 B1) and EP 0 474 763, the catalyst acts as a chlorine reservoir. The reaction cycle consists of a loading step, in which the catalyst which has an oxidic active component phase is laden with hydrogen chloride, and a subsequent regeneration step, in which an oxygen-containing gas flows over the catalyst and regenerates the latter, chlorine being liberated.

In the novel process involving a nonsteady-state reaction, the novel bismuth-based catalyst acts as an oxygen reservoir. In the hydrogen-chloride oxidation step, hydrogen chloride is oxidized over the catalyst in the absence of free molecular oxygen to give chlorine and water, the catalyst giving up lattice oxygen and being partially reduced. In the subsequent regeneration step, an oxygen-containing gas flows over the partially reduced catalyst, which is reoxidized. In this process, hydrogen chloride is converted quantitatively into chlorine and water as early as the first step, so that hydrochloric acid is no longer present in the product gas and hence the problem of corrosion in the subsequent working-up is reduced. Further advantages over the nonsteady-state Deacon processes according to the prior art arise from the fact that the chlorine is formed directly from hydrogen chloride and is not stored in between. The problems arising from the formation of volatile chloride intermediates of the catalysts, such as catalyst discharge, decrease in activity and contamination of the subsequent line sections, are thus avoided. Furthermore, there are no problems which occur as a result of the adsorption of hydrogen chloride onto the carrier and which lead to contamination of the product gas, since, as stated above, hydrogen chloride is quantitatively converted as early as the first stage of the process.

Owing to the abovementioned very high oxidation activity of the catalyst, due to the proportions of oxidation state +5 present, the oxidation of the hydrogen chloride takes place at high reaction rates even at low temperatures, so that rapid conversion occurs even at room temperature. There are therefore surprising simplifications in terms of process engineering, since the thermodynamic equilibria are rapidly reached, resulting in lower requirements with regard to thorough mixing and residence time.

The initial temperature of the hydrogen chloride oxidation is from 0° C. to 700° C., preferably from 25° C. to 600° C. During the reaction, the temperature may fluctuate slightly owing to heat effects. Since the hydrogen chloride oxidation is highly exothermic with enthalpy of reaction $\Delta/H_R$ (700 K) of −58.6 kj/mol, adequate heat removal must be ensured. Since, as stated above, the novel catalysts serve as an oxygen reservoir and hence no volatile chlorides are formed, and they are also mechanically and thermally stable, local overheating up to about 150 K is tolerated without loss of elements.

The hydrogen chloride concentration in the feed stream is from 1 to 100% of hydrogen chloride, high concentrations being advantageous. Hydrogen chloride concentrations of from 10 to 100% are preferably used.

Between the oxidation and the regeneration step, the reactor is preferably flushed free of hydrogen chloride by means of a flushing gas. The flushing gases used are nitrogen, noble gases, carbon dioxide or mixtures thereof.

The partially reduced catalyst is regenerated with oxygen-containing gases, air, oxygen-enriched air, pure oxygen or nitrous oxide preferably being used.

The three steps comprising oxidation of hydrogen chloride to chlorine, flushing and regeneration of the catalyst can be carried out by either the cocurrent or the countercurrent method. In general, flow reversal between oxidation and regeneration is employed in order to achieve advantageous heat transfer. The gas flows may differ in the individual steps. It is also possible to use flow gradients or flow stages in the oxidation and regeneration, in order to regulate the residence time and the concentration of substances in the gas phase. It is also possible to admix a carrier gas in the form of a gradient or in discrete stages in order to implement a residence time ramp.

Chlorine can be isolated from the product gas by, for example, condensation, absorption in solvents and/or absorption by means of pressure change.

Local excessive hydrogen chloride concentrations, and associated with this, the complete reduction of the novel catalyst must be avoided for the reasons described above. In the steady-state reaction, it is therefore advantageous to u se a fixed-bed, fluidized-bed or moving-bed reactor and to carry out the reaction under an oxygen excess and at a temperature at which the reoxidation takes place sufficiently rapidy. However, since the removalt of heat in the fixed bed presents problems, the fluidized bed and moving bed are preferred. Fluidized-bed reactors are particularly suitable. Since the solid phase and hence the catalyst in the fluidized bed exhibit roughly the residence time behavior of an ideal stirred kettle, ie. are very thoroughly back-mixed, virtually uniform reduction of all catalyst particles takes place. The average degree of reduction of the catalyst particles is therefore invariant as a function of time and space. A decrease in temperature in the steady-state reaction results in an equilibrium shift toward high conversions. However, the regeneration with oxygen requires a higher temperature for achieving adequate reoxidation rates.

Preferred temperature ranges for the steady-state process are from about 30 to about 700° C. for the oxidation and from about 500 to 800° C. for the regeneration.

Two variants are possible for the technical implementation of the novel nonsteady-state process, separation of the two steps, oxidation and regeneration, either in space or in time, if necessary interrupted by a flushing process as a further step.

In the spatial separation, a moving bed or fluid bed or a circulating fluidized bed is employed, for example with the use of a riser reactor, so that, after removal of the resulting reaction products of chlorine and water, the catalyst particles from the hydrogen chloride oxidation zone are fed to a separate regeneration reactor in which the reoxidation is carried out. The regenerated catalyst is then recycled to the hydrogen chloride oxidation zone. The process is continuous and cyclic since the catalyst is continuously circulated. The catalyst is exposed to high mechanical stresses and must therefore have sufficient hardness. This requirement is met by the novel catalysts.

The separation of the two steps in terms of time can be realized by means of a fixed bed or a conventional fluidized bed by switching periodically between the hydrogen chloride feed and the regeneration step, possibly after a flushing phase with inert gas. A plurality of alternately operated fixed-bed or fluidized-bed reactors can be coupled to give an integrated heat system.

In the nonsteady-state procedure, a fixed-bed arrangement is less promising since the degree of reduction of the catalyst is not uniform but varies with the tube length. Since the catalyst zones on the reactor inlet side are continuously in contact with HCl during the entire cycle time, there is a danger here, after complete reaction of the Bi +5 centers, that undesirable secondary chlorination reactions will take place before the HCl front has reached the zones on the reactor outlet side, whose oxygen reservoir is still fully charged. Multiple feeding of HCl and/or oxygen for establishing very homogeneous concentration distributions is possible but entails a high cost. The procedure using less than the stoichiometric amount of HCl in the fluidized bed or in the moving bed is therefore particularly preferred.

In the fluidized bed, the total catalyst material is uniformly reduced owing to the thorough mixing of the particles. With termination of the HCl oxidation and change over to regeneration at the proper time, the average Bi oxidation state can be kept above +3. The undesirable secondary reactions described above are thus prevented. This embodiment of the novel process using less than the stoichiometric amount of HCl requires relatively large amounts of catalyst for achieving high space-time yields, although said amounts do not represent a decisive cost factor for the novel process since the novel catalysts can be economically prepared.

Another preferred variant is based on the use of a moving bed. Circulating fluidized beds in the form of a riser or dropper reactor are explicitly included therein. The hydrogen chloride feed to the moving bed may be cocurrent or countercurrent.

In the riser, for example, the catalyst particles are entrained by the HCl gas and are transported in the direction of flow. The residence times in the riser are usually very short and the solids content very high so that the catalyst is by no means deeply reduced, but the degree of utilization tends to be low. The oxygen reservoir is therefore always well filled so that there is no danger of irreversible chlorination.

In the dropper, the catalyst particles are transported with the use of gravitational force. Otherwise, the mode of operation of the dropper is comparable to that of the riser.

The mode of operation of the novel process using a moving-bed reactor is described below. HCl gas flows over a catalyst bed, resulting in the formation of a gradient of the degree of reduction of the catalyst. At the beginning of the bed, the catalyst is more greatly reduced than in the downstream zones. At the end of the bed, scarcely any further oxygen is removed from the oxygen reservoir. To achieve quantitative hydrogen chloride conversion, further feed of still unreduced catalyst is required. When the degree of oxidation in the initial zone has fallen to such an extent that regeneration is necessary in order to prevent the secondary reaction, only this zone is removed from the reaction zone, continuously or in discrete steps, in order subsequently to be reoxidized externally. At the end of the bed, fresh catalyst is added and the HCl oxidation is continued. Example 1 according to the invention shows that, by means of this procedure, the chlorination of the catalyst can be completely avoided and the partially reduced catalyst can be reversibly regenerated, ie. has the original activity and the same Bi +5 content after reoxidation as before.

The present invention furthermore relates to the use of the abovementioned catalysts in oxidation and dehydrogenation reactions under heterogeneous catalysis, in particular those reactions which take place in the gas phase. Examples of such reactions are the oxidation of hydrogen halides to the halogens, oxidative methane coupling, dehydrocoupling of substituted toluenes to give the corresponding stilbenes, oxidative dehydrogenation of cycloalkanes to give aromatics, oxidative dehydrogenation of vinylcyclohexane to give ethylbenzene/styrene and epoxidation of olefins.

The preparation and use of the novel catalysts will be described in more detail below with reference to the following, nonrestricting examples.

EXAMPLE 1
Preparation of a Barium Bismuth Oxide Catalyst 5.42 g of $Bi_2O_3$ and 5.67 g of $BaCO_3$ are homogenized in acetone and calcined in the air at 800° C. in a chamber furnace. The reaction conditions are chosen as follows: heat-up rate 2° C./min., holding time at 800° C. 3 h, cooling rate 1° C./min. In order to ensure that the preparation is homogeneous, it is then ground in a mortar and again treated under the abovementioned reaction conditions.

The catalyst is characterized by means of powder X-ray diffraction. The exact heavy atom composition is determined by X-ray fluorescence spectroscopy and chemical analysis. The content of Bi +5 is determined by iodometric titration and differential thermal analysis (DTA/TG). The catalyst consists of a single phase and has a rhombohedrally distorted perovskite superlattice. It is thermally and mechanically stable and can be calcined up to about 900° C. without destruction of the phase (reversible $O_2$ elimination takes place from about 550° C.). At the same time, the following reversible phase transformations take place:

620° C.—Formation of a perovskite phase

750° C.—Transformation into a phase having the tetragonal perovskite structure

820° C.—Phase transformation into a tetragonal phase having a perovskite superlattice The last-mentioned phase no longer contains Bi(5).

The catalyst is stable in air, nonvolatile and insoluble in alkalis but soluble in aqueous acids.

The catalyst has the composition $BaBi_{0.81}O_{2.6}$. The Bi +5 content is 47.85% (based on the total bismuth content) and is determined by iodometric titration according to Bunsen.

The color of the oxidized catalyst is dark brown. The reduced phase is dark red. The preparation obtained in the solid-state reaction has a porous structure.

EXAMPLE 2
Preparation of chlorine from gaseous dry dilute HCl in a moving-bed reactor in an unsteady-state reaction 10 g of the catalyst are introduced in four equal portions into a water-cooled reaction tube. Glass wool is used as a barrier between the layers. The catalyst is cooled to room temperature by means of water. 100 ml of HCl diluted with 300 ml of argon are injected by means of a piston sampler. The chlorine formed in the reaction is passed in a gentle argon stream into a receiver containing ice-cooled KI solution. The $I_2$ formed is titrated with 0.1 N thiosulfate solution using starch as an indicator.

From the $4.4 \times 10^{-3}$ mol of HCl gas used, the calculated theoretical consumption of thiosulfate solution is 43.82 ml, corresponding to $2.2 \times 10^{-3}$ mol of $Cl_2$. The actual consumption is 43.52 ml of thiosulfate solution, corresponding to $2.18 \times 10^{-3}$ mol of $Cl_2$. This indicates virtually complete (99.3%) conversion of HCl.

Samples of the catalyst sections 1 and 2 reacted with HCl are tested by means of $AgNO_3$ solution to determine if any chlorides have formed. The test is negative. After further reaction with 100 ml of dilute HCl (99.5% conversion), the total catalyst material is investigated for chlorides. Once again, no chlorides are detectable.

For regeneration, the catalyst material is calcined in the air at 550° C. in a chamber furnace under the following reaction conditions:

Heat-up rate 10° C./min, holding time at 550° C. 2 hours, cooling rate about 3° C./min. A subsequently performed iodometric titration indicates complete regeneration of the catalyst.

The reaction with 2×100 ml of dilute HCl is repeated once more under the above conditions. The reaction takes place with 99.4 and 99.6% yield respectively.

As the experiment shows, complete conversion of HCl to chlorine can be achieved by the choice of a moving bed and dilution of the HCl (the determination of the resulting amount of chlorine by iodometric titration is carried out with an error of about ±0.5%). The catalyst can be completely regenerated. The formation of barium and bismuth chlorides in the presence of less than stoichiometric amount of HCl is not observed, ie. the irreversible chlorination of the catalyst can be effectively prevented by means of a moving bed.

Removal of the resulting partially reduced barium bismuth oxide catalyst from the reaction space at the proper time is important since otherwise a further reaction with HCl takes place. The individual moving-bed zones are preferably withdrawn from the reactor and regenerated even before the average Bi oxidation state has decreased to +3.

Cooling of the catalyst to room temperature, as achieved by using a water-cooled reactor tube, is not absolutely essential. It serves only to demonstrate the high catalyst activity.

COMPARATIVE EXAMPLE 1
Preparation of Chlorine From Aqueous HCl Solution in a Stirred Kettle Reactor Using a Nonsteady-state Reaction 10 g of the catalyst from Example 1 are weighed into a 250 ml three-necked flask. 3.5 ml of concentrated aqueous HCl (37%) are added dropwise in a stream of nitrogen. The chlorine formed in the reaction is passed in a nitrogen stream through a water-cooled reflux condenser into a receiver containing 500 ml of ice-cooled KI solution. The $I_2$ formed is titrated with 0.1 N sodium thiosulfate solution using starch as an indicator.

Theoretical consumption: about 220 ml of thiosulfate solution, corresponding to 2.3 g of Bi (+5) (1.1×10$^{-1}$ mol) or 0.39 g of Cl$_2$.

Actual consumption 157 ml of thiosulfate solution, corresponding to 1.64 g of Bi +5.

The experiment shows that the catalyst is highly active and that the HCl oxidation to chlorine takes place with reduction of the catalyst even at room temperature. Nevertheless, industrial realization of the novel process is not possible under these conditions (aqueous HCl) and with this type of reaction procedure (stirred kettle) since the catalyst is also chlorinated, ie. chlorides form even in the presence of less than the stoichiometric amount of HCl.

COMPARATIVE EXAMPLE 2

Preparation of Chlorine From Gaseous Dry HCl Gas Using an Nonsteady-state Reaction 10 g of the catalyst from Example 1 are introduced into a reaction tube. 200 ml of HCl diluted with 200 ml of Ar are injected by means of a piston sampler. The chlorine formed in the reaction is passed in a gentle argon stream into a receiver containing ice-cooled KI solution. The I$_2$ formed is titrated with 0.1 N thiosulfate solution using starch as an indicator.

From the 8.8×10$^{-3}$ mol of HCl gas used, the calculated theoretical consumption of thiosulfate solution is 87.64 ml, corresponding to 4.4×10$^{-3}$ mol of Cl$_2$.

The actual consumption is 52.43 ml of thiosulfate solution, corresponding to 2.63×10$^{-3}$ mol of Cl$_2$. Thus, the conversion is only 59.8%.

The catalyst sections 1 and 2 reacted with the HCl are tested for chlorides by means of AgNO$_3$ solution.

Cl$^-$ is detectable.

The barium bismuth (+3)oxide formed in the oxidation of the HCl reacts further with HCl in a 2nd stage. In the front region of the catalyst material, the formation of BiOCl and BaCl$_2$ can be detected. The catalyst is irreversibly chlorinated, as in Comparative Example 1.

EXAMPLE 3

Dependence of the crystal structure on the stoichiometry of the heavy atoms barium and bismuth The abovementioned bismuth oxide phases a) to g) can be prepared by using the process conditions described in Example 1 and varying the amounts of Bi$_2$O$_3$ and BaCO$_3$ used.

FIG. 1 shows the ratio of Bi +5 content, based on the total heavy atom content (y axis) to the Ba content, based on the total heavy atom content, for the individual phases. The horizontal line shown indicates the maximum Bi +5 content (27.5 heavy atom %).

Figure 2:
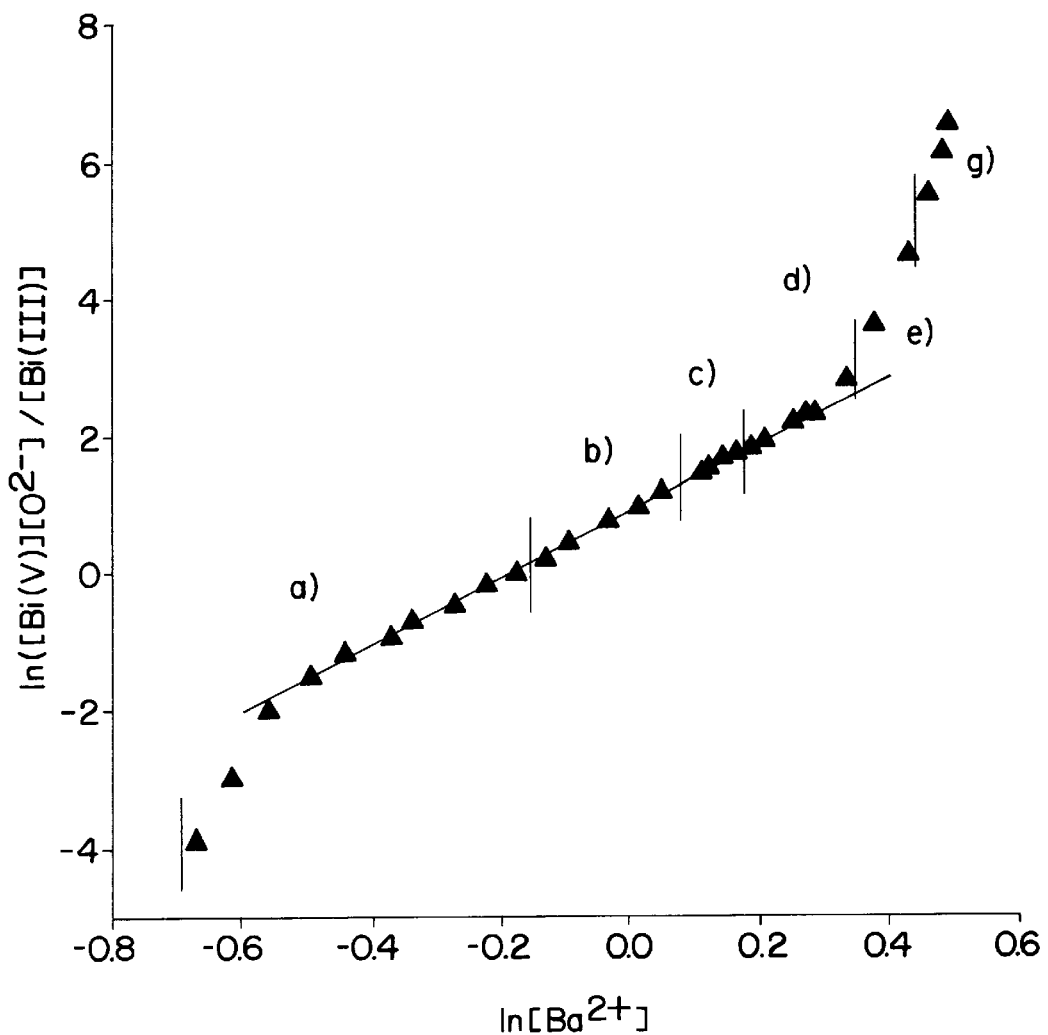
FIG. 2 shows, in double logarithmic plot, the relationship of the Bi+5/Bi+3 redox system (y axis) to the barium content (x axis) for the individual phases.

FIG. 2 shows, in a double logarithmic plot, the relationship of the Bi +5/Bi +3 redox system (y axis) to the barium content (x axis) for the individual phases.

The straight line shown, corresponding to a barium content of from about 30 to about 65 heavy atom %, indicates a region in which the Bi +5 concentration increases as a function of the Ba concentration, according to the following equation:

$$\ln \frac{[Bi(V)][O^{2-}]}{[Bi(III)]} - 4.86(4) - \ln[Ba^{2+}] = K$$

This relationship is analogous to the law of mass action for the redox reaction between Bi +3 and Bi +5:

$$Bi(III) + \tfrac{1}{2}O_2 \leftrightarrows Bi(V) + O^{2-}$$

In the linear region of the double logarithmic plot, indicated by the straight line shown, the four different phases a, b, c and d lying on said line behave like a single homogeneous phase.

The Bi +5 content is determnined by iodomnetric titration according to Bunsen.

We claim:

1. A process for the preparation of chlorine by oxidation of hydrogen chloride, which comprises (a) bringing a catalyst composition into contact with hydrogen chloride, wherein the active phase of the catalyst composition contains at least one bismuth oxide compound in which bismuth is present at least partly in oxidation state +5 and the bismuth oxide compound further containing at least one basic metal component stabilizing the oxidation state +5, to oxidize the hydrogen chloride to chlorine and to cause a decrease in the oxidation state of the bismuth and (b) re-oxidizing the catalyst composition before the average oxidation state of the bismuth decreases to +3.

2. A process as claimed in claim 1, wherein the amount of Bi +5 of the catalyst composition is from about 1 to 99% by weight, based on the total bismuth content.

3. A process as claimed in claim 1, wherein the basic metal component of the catalyst composition is selected from the group consisting of alkali metal, alkaline earth metal and rare earth metal.

4. A process as claimed in claim 3, wherein the basic metal component of the catalyst composition is selected from the group consisting of Li, Na, K, Sr, Ba, Cs, Y and La.

5. A process as claimed in claim 1, wherein the active phase of the catalyst composition contains at least one compound of the formula:

KBi$_y$O$_z$ where y is from 0.5 to 2 and z is from 1.25 to 5.5, or of the formula:

BaBi$_y$O$_z$ where y is from 0.17 to 3 and z is from 1.43 to 5.6, in each case at least part of the Bi is present in oxidation state +5.

6. A process as claimed in claim 5, wherein the active phase of the catalyst composition contains at least one compound of the formula KBi$_y$O$_z$, wherein the quotient y/z is from about 0.4 to about 0.36.

7. A process as claimed in claim 5, wherein the active phase of the catalyst composition contains at least one compound of the formula BaBi$_y$O$_z$, wherein the quotient y/z is from about 0.12 to about 0.54.

8. A process as claimed in claim 1, wherein the active phase of the catalyst composition furthermore contains at least one promoter selected from elements of main groups 1, 2 and 4 and from subgroup 4 and/or 6 of the Periodic Table.

9. A process as claimed in claim 1, wherein the catalyst composition a) is in the form of an unsupported catalyst;

b) has been mixed with a binder or c) has been applied to an inert carrier.

10. A process as claimed in claim 1, wherein the process is a steady state procedure, said hydrogen chloride together with an oxygen-containing gas are brought into contact with the catalyst composition and hydrogen chloride; oxidized to chlorine.

11. A process as claimed in claim 10, wherein the catalyst composition is used as a fixed bed, fluidized bed, moving bed or fluid bed.

12. A process as claimed in claim 1, wherein the process is a non-steady-state procedure, and in step a) the catalyst composition is brought into contact with an oxygen-free gas containing the hydrogen chloride, the hydrogen chloride is oxidized to chlorine and the reaction products are removed, and in step b), at least some of the total catalyst composition is reoxidized in the presence of an oxygen-containing gas.

13. A process as claimed in claim 12, wherein the catalyst composition is used as a fluidized bed, moving bed or fluid bed.

* * * * *

UNITED STATES PATENT AND TRADEMARK OFFICE
CERTIFICATE OF CORRECTION

PATENT NO. : 6,197,275 B1
DATED : March 6, 2001
INVENTOR(S) : Hagemeyer et al.

It is certified that error appears in the above-identified patent and that said Letters Patent is hereby corrected as shown below:

<u>Column 13, claim 10,</u>
Line 2, "chloride; oxidized" should be -- chloride is oxidized --.

Signed and Sealed this

Second Day of October, 2001

Attest:

NICHOLAS P. GODICI
Attesting Officer *Acting Director of the United States Patent and Trademark Office*